(12) United States Patent
Forman et al.

(10) Patent No.: US 9,712,789 B2
(45) Date of Patent: Jul. 18, 2017

(54) METHOD AND APPARATUS TO GENERATE IMAGE DATA

(71) Applicant: Siemens Aktiengesellschaft, Munich (DE)

(72) Inventors: Christoph Forman, Erlangen (DE); Michael Zenge, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 498 days.

(21) Appl. No.: 14/244,028

(22) Filed: Apr. 3, 2014

(65) Prior Publication Data

US 2015/0015691 A1 Jan. 15, 2015

(30) Foreign Application Priority Data

Apr. 3, 2013 (DE) ........................ 10 2013 205 832

(51) Int. Cl.
| | |
|---|---|
| *H04N 7/00* | (2011.01) |
| *H04N 7/18* | (2006.01) |
| *A61B 5/055* | (2006.01) |
| *G01R 33/565* | (2006.01) |
| *G01R 33/567* | (2006.01) |
| *G06K 9/00* | (2006.01) |
| *A61B 5/00* | (2006.01) |
| *G01R 33/48* | (2006.01) |

(52) U.S. Cl.
CPC .............. *H04N 7/18* (2013.01); *A61B 5/055* (2013.01); *A61B 5/7292* (2013.01); *G01R 33/5676* (2013.01); *G01R 33/56509* (2013.01); *G06K 9/00362* (2013.01); *G01R 33/4826* (2013.01)

(58) Field of Classification Search
CPC .. A61B 5/05; G06T 5/00; G06T 11/00; G06K 9/00
See application file for complete search history.

(56) References Cited

U.S. PATENT DOCUMENTS

| | | | | |
|---|---|---|---|---|
| 6,103,350 A | * | 8/2000 | Grangeat | G06T 5/002 351/205 |
| 6,192,265 B1 | * | 2/2001 | Carlsen | G06T 11/005 324/309 |
| 7,630,528 B2 | * | 12/2009 | Kohler | G06T 11/006 378/4 |

(Continued)

OTHER PUBLICATIONS

Bordes et al SGD-QN: Careful Quasi-Newton Stochastic Gradient Descent et al; 10(Jul):1737-1754, 2009.*

(Continued)

*Primary Examiner* — Frank Huang
(74) *Attorney, Agent, or Firm* — Schiff Hardin LLP (57) ABSTRACT

In a method and apparatus for the generation of image data of a moving subject, raw data are initially acquired for a region comprising the subject at different measurement points in time in different movement phases of the subject. A reconstruction then takes place of multiple interim image data sets of the subject from the raw data that are respectively associated with different movement phases of the subject. Deviation data are then determined between the interim image data sets of the different movement phases of the subject, and the reconstruction of image data from raw data of different movement phases then takes place under consideration of the deviation data.

14 Claims, 7 Drawing Sheets

(56) References Cited

U.S. PATENT DOCUMENTS

| | | | |
|---|---|---|---|
| 7,899,227 B2* | 3/2011 | Fenchel | G06F 19/321 382/128 |
| 8,379,946 B2* | 2/2013 | Greiser | A61B 5/055 382/128 |
| 2006/0241379 A1* | 10/2006 | Greiser | A61B 5/055 600/410 |
| 2007/0159174 A1 | 7/2007 | Oshio | |
| 2009/0010514 A1 | 1/2009 | Kimura | |

OTHER PUBLICATIONS

"Free-Breathing Whole-Heart Coronary MRA With 3D Radial SSFP and Self-Navigated Image Reconstruction," Stehning et al., Magnetic Resonance in Medicine, vol. 54 (2005), pp. 476-480.

"Respiratory Self-Navigation for Whole-Heart Bright-Blood Coronary MRI: Methods for Robust Isolation and Automatic Segmentation of the Blood Pool," Piccini et al., Magnetic Resonance in Medicine, vol. 68 (2012), pp. 571-579.

"Submillimeter Three-dimensional Coronary MR Angiography with Real-time Navigator Correction: Comparison of Navigator Locations," Stuber et al., Radiology, vol. 212, No. 2 (1999), pp. 579-587.

"Minimization of Respiratory Motion Artifacts for Whole-Heart Coronary MRI: A Combination of Self-navigation and Weighted Compressed Sensing Reconstruction," Forman et al., Proceedings of the 20th Annual Meeting ofISMRM, Melbourne, Australia, (2012), p. 1160.

"Symmetric diffeomorphic image registration with cross-correlation: Evaluating automated labeling of elderly and neurodegenerative brain," Avants et al., Medical Image Analysis, vol. 12 (2008), pp. 26-41.

"3D Radial Sampling and 3D Affine Transform-based Respiratory Motion Correction Technique for Free-breathing Whole-Heart Coronary MRA with 100% Imaging Efficiency," Magn. Reson. Med., vol. 65, No. 5 (2011), pp. 1269-1277.

"Respiratory Self-Gated Four-Dimensional Coronary MR Angiography: A Feasibility Study," Lai et al., Magn. Reson. Med., vol. 59, No. 6 (2008), pp. 1378-1385.

* cited by examiner

FIG 8

METHOD AND APPARATUS TO GENERATE IMAGE DATA

BACKGROUND OF THE INVENTION

Field of the Invention

The present invention concerns a method to generate image data (in particular magnetic resonance exposures) of a subject moving inside a body, for example an organ, parts of an organ or an arbitrary target structure inside a human or animal. Moreover, the invention concerns an image data generation device to generate image data of a subject moving inside a body, as well as a magnetic resonance system with such an image data generation device.

Description of the Prior Art

In order to obtain image data (magnetic resonance exposures) from a region of the inside of the body of an examination subject in magnetic resonance tomography, the body or the body part to be examined must initially be exposed to an optimally homogeneous, static basic magnetic field (most often designated as a $B_0$ field). Nuclear spins in the subject are thereby aligned parallel to the direction of the $B_0$ field (typically designated as the z-direction). Moreover, radio-frequency pulses are radiated into the examination subject with radio-frequency antennas, the frequency of the radio-frequency pulses being at or approximately at the resonance frequency (known as the Larmor frequency) of the nuclei to be excited (normally hydrogen nuclei) in the basic magnetic field. These radio-frequency pulses are therefore designated as magnetic resonance radio-frequency pulses in the following. The magnetic flux density of these radio-frequency pulses is typically designated with $B_1$. By means of these radio-frequency pulses, nuclear spins of the atoms in the examination subject are excited such that they are deflected by an amount known as an "excitation flip angle" (generally shortened to "flip angle") out of their steady state (parallel to the basic magnetic field $B_0$). The nuclear spins then initially precess around the z-direction and relax again bit by bit. The in-phase revolution of the microscopic spins around the precession cone can be viewed as a macroscopic nuclear magnetization in the x/y plane (orthogonal to the z-direction). The magnetic resonance signals generated in this relaxation of the nuclear magnetization are acquired as raw data by radio-frequency reception antennas. Magnetic resonance images of the examination subject are reconstructed on the basis of the acquired raw data. Spatial coding of the magnetic resonance signals takes place with the use of rapidly switched (activated) gradient magnetic fields that are superimposed on the basic magnetic field during the emission of the magnetic resonance radio-frequency pulses and/or the acquisition of the raw data. In the data acquisition, the raw data are initially associated with frequency domain (known as k-space). The reconstruction of the image data then takes place by means of a Fourier transformation of the raw data of k-space into the image data domain (spatial domain).

Particularly when image data of a complete organ should be generated (i.e. when either volume data or a number of densely adjoining slice images should be acquired that cover the complete region in which the organ is located) a longer measurement time is required. This is a problem if a moving organ is being examined (the heart, for example). The heart not only performs its own cyclical movements due to the heart beat, but also is additionally subject to movement due to the breathing of the patient. If raw data were simply acquired during the different movement cycles, and image data were then reconstructed from this raw data, this would lead to significant movement artifacts (for example smearing in the images), such that the generated images could often not be used for a reasonable diagnosis.

One possibility to avoid such artifacts is to acquire raw data only in a defined movement phase of the organ (heart), for example to trigger the raw data acquisition in a suitable manner. For example, with regard to the heart movement it is possible to implement such a triggering at a defined heart phase with the use of an EKG. The data are preferably acquired in the diastolic phase, since in this phase the heart movement is minimal for a relatively long time. This diastolic phase lasts approximately 100 ms. In many acquisition methods (in particular in the acquisition of the complete volume or a number of densely placed slices that cover the heart), a duration of 100 ms is not sufficient to acquire all raw data. This particularly applies in the acquisition of raw magnetic resonance data. Therefore, raw data sets or, respectively, segments of k-space must respectively be acquired in the matching cardiac phase in order to fill k-space with the necessary raw data before the image data of the volume or the desired slices are then reconstructed in the manner described above. However, the breathing movement that is additionally superimposed on the movement of the heart can lead to the situation that the heart can be situated at different locations in the body (for example in the diastolic phases of successive cardiac cycles) depending on the current movement phase of the breathing cycle. In principle, it would naturally be possible to also monitor the breathing cycle with appropriate devices and to additionally trigger on the breathing cycle. In such a case, however, raw data would only be acquired when the desired cardiac phase and the desired breathing phase randomly occur together. This would lead to a total measurement duration that is much too long, and therefore such measurement methods are not acceptable in practice.

For example, a method for time windowing of angiographic magnetic resonance acquisitions under consideration of breathing phases is described in the article "Respiratory Self-Gated Four-Dimensional Coronary MR Angiography: A Feasibility Study" by Peng Lai et al. in Magn. Reson. Med., Vol 59, 2008, No. 6, P. 1378-1385.

In order to fill a sufficiently large k-space volume with measurement data so as to be able to reconstruct from these a three-dimensional volume of a complete organ (such as the heart), it is consequently necessary to acquire raw data at different measurement points in time in different movement phases of the subject. This means that the scan patterns are deconstructed into different segments, and that the segments or raw data sets are most often read in directly successive cardiac cycles that can be located in different movement phases of the subject due to the breathing. A typical scan pattern is known as a phyllotactic, spiral-shaped pattern, as will be explained below in further detail. In this pattern, readout points lie on a spoke-like trajectory as seen in a plane (for example the x/y plane) through k-space, wherein the spokes proceed outwardly from the k-space center and are curved in a spiral shape, for example. The individual readout (entry of raw data into) of each plane of such spokes proceeds plane-by-plane in a straight line in the direction (for example the z-direction) orthogonal to the planes. For example, a complete filing of all planes among the z-direction through k-space is considered as a readout process.

However, the problem exists that the raw data originate from different movement phases (in particular breathing phases), independently of in which segments the raw data are acquired. A correction within the reconstruction method is therefore required, which compensates again for these image disruptions caused by the different movement phases, and thus ensures that no movement artifacts appear in the finished image data.

In the article "3D Radial Sampling and 3D Affine Transform-based Respiratory Motion Correction Technique for Free-breathing Whole-Heart Coronary MRA with 100% Imaging Efficiency" by Himanshu Bath et al. in Magn. Reson. Med., Vol. 65, 2011, No. 5, P. 1269-1277, it is proposed to generate respective image data from the raw data from different movement phases, and to then generate a movement-corrected image from these image data via suitable summation. In DE 197 13 846 A1 and DE 697 21 900 T2, corrected image data are similarly created from previously reconstructed image data.

SUMMARY OF THE INVENTION

An object of the present invention is to provide a method to generate image data, as well as an image data generation device, which allow the use of raw data from different movement phases but wherein movement artifacts are nevertheless reduced (ideally are even completely avoided).

In the method according to the invention, an acquisition of raw data initially takes place for a region that includes the subject of interest at various measurement points in time in different movement phases of the subject. The acquisition of the raw data can be the direct acquisition of such raw data at the magnetic resonance system and/or the receipt, via a suitable interface, of raw data already acquired at various (earlier) measurement points in time at an arbitrary magnetic resonance system.

For example, the raw data acquired at a measurement point in time can be the raw data set acquired at the defined measurement point in time, or the acquired segment in k-space. The acquisition of such a raw data set or segment requires a defined (short) time period, such that, as used herein, the term "measurement point in time" is always a short "measurement time segment", for example the approximately 100 ms in the diastolic phase given the acquisition of a heart.

A reconstruction of multiple interim image data sets of the subject from the acquired raw data then initially takes place, wherein these interim image data sets are respectively associated with different movement phases of the subject. The same raw data are used for this interim reconstruction as are also required later, together with additional raw data, for the reconstruction of the desired finished (diagnostic) image data. In other words: the interim image data sets differ from the later image data sets not by containing different raw data, but rather by containing only a portion of the total raw data (for example only raw data of a defined movement phase). Additionally or alternatively, for raw data of different movement phases can be used with different weightings in order to make the interim image data sets match the movement phases.

Furthermore, a determination of deviation data takes place, for example by determining deformation fields (also called movement fields) between the interim image data sets of the different movement phases of the subject. In principle, it is sufficient for the deviation data of the interim image data sets relative to a reference image data set to be determined, because then the deviation data between the different interim image data sets are thus also indirectly defined as well.

Finally, a reconstruction of the desired image data from raw data of different movement phases takes place under consideration of these deviation data. All acquired raw data from all movement phases are advantageously included in order to have an optimally large database for reconstruction of the image data. Depending on the reconstruction method and type of deviation data, the previously determined deviation data can be used directly, or (for example) additional deviation data initially derived from these can also be calculated. For example, the deviation data can initially be inverted or, respectively, inverse deformation fields can also be calculated in addition to the deformation fields, which inverse deformation fields then likewise enter into the reconstruction.

A basic difference between the inventive method and the aforementioned method of Bath et al. is that desired image data are not determined from the previously determined image data of the individual movement phases (as in the Bath et al. procedure), but rather the reconstruction of the desired image data takes place directly from raw data in that the measured raw data are used again and the deviation data additionally enter into the reconstruction. The method according to the invention thus also allows movement-corrected image data that are based on a relatively large amount of raw data to be generated without significant additional effort, even when only a small number of raw data are present in the different movement phases and the movement phases lead to strong deviations of the subject bearing and/or shape. Overall, volume image data of a moving subject can thus also be generated with sufficiently high image quality and reduced movement artifacts in shorter measurement time periods than before.

An image data generation device according to the invention that operates according to the inventive method has a raw data acquisition unit for receiving raw data representing a region of an examination subject including the object of interest, wherein the raw data have been acquired at different measurement points in time in different movement phases of the subject. As mentioned above, the image data generation device can be an interface that accepts the raw data from a memory or from another unit, for example.

Furthermore, the image data generation device requires an interim image reconstruction unit that is designed in order to reconstruct multiple interim image data sets that are respectively associated with different movement phases of the subject.

Moreover, a deviation data determination unit is required that is designed in order to determine deviation data between the interim image data sets of different movement phases of the subject or, respectively, relative to reference image data sets, as explained above.

A complete reconstruction unit is additionally required, which is designed in order to reconstruct the desired image data from raw data of the most different movement phases under consideration of the deviation data. In principle, this complete reconstruction unit can be the same reconstruction unit as the interim image reconstruction unit, for example with a suitable optimizer that calculates the image data matching the raw data to be measured in a numerical optimization method, to which other input parameters and/or other target functions are provided as necessary. These possibilities are explained in detail below.

Via an image data interface of the image data generation device, the image data can then be provided as an output to any arbitrary component, for example to be stored in a memory and/or shown at a monitor and/or to be transmitted via a network to a finding station or an external storage, etc.

An image data generation device according to the invention can be integrated as a component into a magnetic resonance system according to the invention.

In addition to such an image data generation device according to the invention, this magnetic resonance system typically has: a measurement space in which the patient or examination subject is located during the measurement, a basic field magnet system with which a basic field magnetic field is typically applied in the measurement space, a transmission antenna system, a gradient system including multiple gradient coils, a reception antenna system, and a control device that serves to control the basic field magnet system, the RF transmission antenna system, the gradient system and the RF reception antenna system.

The image data generation device according to the invention also can be a part of another tomography system. The image data generation device can likewise be realized at a different, separate device that, for example, is connected via a network with a suitable computer tomography system, or can receive the raw data in a different way. Furthermore, it is possible for the image data generation device and its various components (in particular the interim image reconstruction unit, the deviation data determination unit and the complete reconstruction unit) to be realized in the form of software components at a suitable computer or at one or more suitable processors. This likewise applies to the raw data interface and possibly an image data interface, wherein these interfaces can be designed in part as hardware interfaces or combined software/hardware interfaces. However, the interfaces can similarly also be purely software interfaces if the data have merely been accepted from other software components.

A realization largely in software has the advantage that image generation devices that have already previously been in use can also be retrofitted simply by a software update in order to operate in the manner according to the invention. Thus, the present invention also encompasses a non-transitory, computer-readable data storage medium encoded with programming instructions that can be loaded directly into a memory of a programmable image generation device, with program segments that cause all steps of the method according to the invention to be implemented when the instructions are executed in the image generation device.

In a particularly preferred embodiment of the method, the raw data are weighted differently, depending on the movement phase in which they were acquired, in the reconstruction of different interim image data sets. This ensures that raw data that were acquired in a movement phase used to determine interim image data sets of this defined movement phase, while still allowing additional raw data to be added, for example with appropriately lower weighting, in order to also increase the database for the interim image data sets. It is not a necessity for the later determination of the deviation data that the raw data be determined exclusively from the associated movement phase itself. Rather a somewhat larger database leads to better results.

The weighting of the raw data preferably takes place depending on a distance from a defined movement phase for which the interim image data sets are currently reconstructed. As used herein, "distance" is a chronological duration (spacing) within a movement cycle (breathing cycle, for example), but also can be a spatial distance that, for example, can be determined from a deviation of the raw data or from image data reconstructed therefrom.

In a preferred method, the raw data are associated with different movement phase classes, meaning that the raw data are classified or sorted. In this case, for example, the distance of the raw data from a defined movement phase can also be understood as a separation of the movement phase classes from one another, for example how closely the movement phase classes are to one another, or how many other movement phase classes lie between them. For example, the interim image data sets can then be reconstructed for different movement phase classes, and in the reconstruction the raw data can then be weighted depending on a movement phase class associated with them. The further that the movement phase class of the raw data is distant from the movement class for which the interim image data set should be reconstructed, the lower the weighting.

In the reconstruction of the interim image data sets for a defined movement class, according to a weighting function (advantageously a Gaussian function or a similar function) the raw data of the appertaining movement phase class (i.e. the raw data associated with the appertaining movement phase class) with a higher weighting and the raw data of other (for example directly or indirectly adjacent) movement phase classes with a lower weighting in relation to the raw data of the appertaining movement phase class for which the reconstruction of the interim image data takes place are thus used.

An iterative numerical optimization method can advantageously be used to reconstruct the image data and/or the interim image data sets. A nonlinear optimization method is particularly preferably used, in particular a quasi-Newton method as is explained in detail later. For example, for this purpose the deviation data can initially be inverted and then be used in a target function of the optimizer in the later reconstruction of the image data under consideration of said deviation data.

The classification of the raw data in the different movement phase classes can take place in different ways.

One possibility is to acquire data are known as special navigator raw data from which navigator images are then generated. A volume is normally acquired with these navigator images, in which volume a breathing movement can be detected particularly well. For example, given cardiac exposures the diaphragm can be observed in the navigator exposure since the liver/lung transition is very easy to detect because the liver appears relatively light in the images (due to being filled with fluid) and the lung appears relatively dark in the images (due to being filled with air). With the knowledge of the current breathing position or breathing phase that is determined from the navigator images, the respective raw data and/or the image data of the desired subject that are acquired immediately after the acquisition of the raw navigator data are then corrected with regard to the breathing phase. However, to implement this method the acquisition of additional raw navigator data is required, which requires additional expenditure and in particular additional measurement time.

In a preferred version of the method, the same position overview data are generated for the different measurement points in time on the basis of at least a portion of the raw data. This means that, for the position overview data, only raw data are used that themselves are also used for reconstruction of the image data of the desired FoV or, respectively, subject, such that no additional navigator measurement is required. In order to generate position overview data for the different measurement points in time on the basis of at least a portion of the raw data, the image data generation device can have an overview data generation unit. The position overview data can be image data that allow a detection of the current movement phase in some manner. In principle, these can thereby be three-dimensional, two-dimensional or even just one-dimensional data.

An association of the raw data with the different movement phase classes then takes place based on these position overview data.

To create simple one-dimensional position overview data, respective raw data along a line (central readout process), for example in the z-direction (thus in the direction of the longitudinal axis of the body), through the center of k-space are preferably acquired in the acquisition of segments of k-space. This is particularly suitable when, as mentioned, raw data entered into k-space are according to a phyllotactic, spiral-shaped pattern in order to reconstruct a volume. In addition to the central readout process, raw data must then still be acquired only along additional lines lying parallel to the central line, for example along readout processes in the z-direction that proceed through points, within an x/y plane orthogonal to the z-direction, that lie on a spiral-shaped, outwardly traveling trajectory.

The central readout process is advantageously selected so as to proceed in a primary movement direction of the organ. A one-dimensional projection in the primary movement direction of the organ—for example in the SI direction (SI=Superior-Inferior, thus along the longitudinal axis of the body or in the z-direction) given the heart—can then be generated for each raw data set, or each segment, on the basis of the raw data acquired along the central readout process traveling through the k-space center. These projections, known as "SI projections" concerning one-dimensional image data, namely the projections of the image data of the entire acquired volume (in the FoV=Field of View; viewing area) traveling along the z-direction onto the z-axis. The breathing position can respectively be determined from these SI projections without navigators, and a correction of the raw data and/or image data can take place in the reconstruction. This technique is described by Piccini D. et al. in "Respiratory Self-Navigation for Whole-Heart Bright-Blood Coronary MRI: Methods for Robust Isolation and Automatic Segmentation of the Blood Pool", 2012, Magnetic Resonance in Medicine, 68: 571 to 579.

In order to implement the classification, deviation values can advantageously be determined according to predetermined rules for the position overview data of different measurement points in time relative to defined, pre-established reference position overview data. For example, a cross-correlation of the projection data of different SI projections with the projection data of a reference SI projection (in the simplest case, the SI projection of the first measurement point in time) can be implemented for this. The raw data are then associated with different movement phase classes depending on the deviation values. The reference position overview data can in principle be randomly selected. For example, the position overview data at the measurement point in time t=0 (i.e. the position overview data generated first at the beginning of the measurement) can simply be used as reference position overview data (zero reference), and all additional position overview data are then related to these reference position overview data. In principle, however, the position overview data can also initially be analyzed to the effect that particularly suitable reference position overview data are sought, for example those position overview data that have been acquired in a very specific movement phase.

In order to in particular further improve this classification method (also designated as "binning"), the following steps can advantageously be implemented:

A scattering of the position overview data for the individual positions or, respectively, spatial coordinates or position regions, which scattering is dependent on the measurement point in time, is initially determined, for example with a suitable overview image data analysis unit of the image data generation unit. For example, for this purpose, the scattering of the signal value can be determined depending on the time at a defined position within the position overview data. For example, given an SI projection the scattering of the projection signal value can simply be determined at a defined location z, depending on the time. The scattering is thereby measured according to a predetermined measure of scattering. This is preferably the variance.

A selection of spatial test regions within the position overview data subsequently takes place. For this purpose, the image data generation device can have a test region selection unit. Given a one-dimensional projection (for example an SI projection), projection segments can thus be identified as test regions. This selection of the spatial test regions takes place depending on the scattering of the position overview image data in the respective test regions. The position regions or, respectively, position segments can be precisely determined within the position overview data in which the scattering is relatively high, since here it should be possible to detect a movement within the body particularly well.

Furthermore, a determination of trust parameter values for the individual test regions takes place. As explained in detail below, for example, with the use of these trust parameter values it can be established in which of the test regions a movement detection or the precise determination of the movement phases is presumably most reliable. For this, the image data generation device can have a test region selection unit.

The association of the raw data with the movement phase classes can take place under consideration of the trust parameter values of the different test regions. It has turned out that the image quality can in most cases be significantly improved via the identification of different test regions and a monitoring of which of these test regions are particularly well suited to the detection of the movement. While—given an establishment of a (static) test region beforehand—the exposures still in part included movement artifacts in 6 of 10 test subjects, qualitatively equivalent images as they can otherwise be achieved using additional navigator measurements could nevertheless be generated with the described procedure of automatically establishing the optimal test region without using navigator measurements. Very good volume images of the heart can thus be generated with the aid of the method, even without using navigators and consequently with a significant shortening of the total measurement time. This is likely due to the fact that the ideal test regions for different patients or test subjects can lie at different points within the position overview data due to the anatomical differences, and this different position of the optimal test regions can automatically be taken into account by the method according to the invention.

A variety of values can be used as trust parameter values of the individual test regions. In a preferred variant, the trust parameter value of a test region is itself based on a scattering of position overview data within the test region.

For example, for this the classification of the position overview data or, respectively, of the associated raw data with the reference position overview data initially takes place separately on the basis of the deviation values of the position overview data for each of the individual test regions. The determination of the reference position overview data can thereby also take place for the individual test regions.

A spatial scattering value of the position overview data that is dependent on the measurement point in time can then be determined separately for each movement phase class. This scattering value can be determined according to the same rules (i.e. with the same measure of scattering) as the scattering described above according to which the test regions are initially selected, but with the difference that now only the scattering of the position overview data of the respective movement phase class by a mean value calculated from these data still takes place.

A sum of the scattering values of multiple movement phase classes can furthermore then preferably be determined as trust parameter values for a test region. The trust parameter value is advantageously a type of "total deviation value scattering", i.e. the sum of the scattering values of all movement phase classes.

The reconstruction of image data from the raw data then particularly preferably takes place under consideration of the association of the position overview data with the movement phase classes for the those of the test regions in which the trust parameter value is lowest. This means that (for example) the test region in which the sum of the individual scattering values in the movement phase classes is lowest is thus classified as trustworthy. Naturally, depending on determination of the trust value it would also be possible to use the test region in which the trust parameter value is highest.

As mentioned above, the method is advantageously used on examination subjects that are moving due to a breathing motion. The movement phases are the accordingly breathing phases. The examination subject particularly preferably is or, respectively, comprises a heart. However, this does not preclude that the method can also be used on other examination subjects and in other movement workflows, for example to correct swallowing movements or other movements.

DESCRIPTION OF THE PREFERRED EMBODIMENTS

The preferred variant of the method that is described in the following with the use of the figures concerns the acquisition of a complete volume of a heart as an examination subject O in a human body K. The avoidance of movement artifacts in the generation of magnetic resonance exposures of the complete heart O is linked with particular requirements due to the continuous motion of the heart itself, and the breathing movement that is furthermore superimposed upon this. This is explained using FIGS. 1 and 2.

Figure 1:
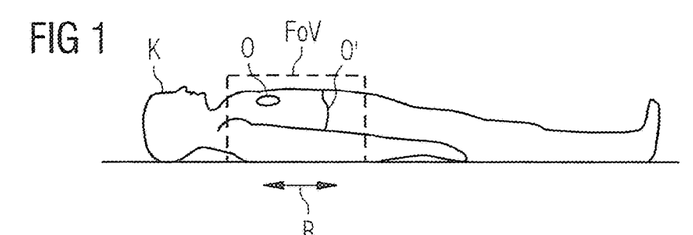
FIG. 1 schematically depicts the SI direction and the position of the heart and the diaphragm in a human body.
Figure 2:
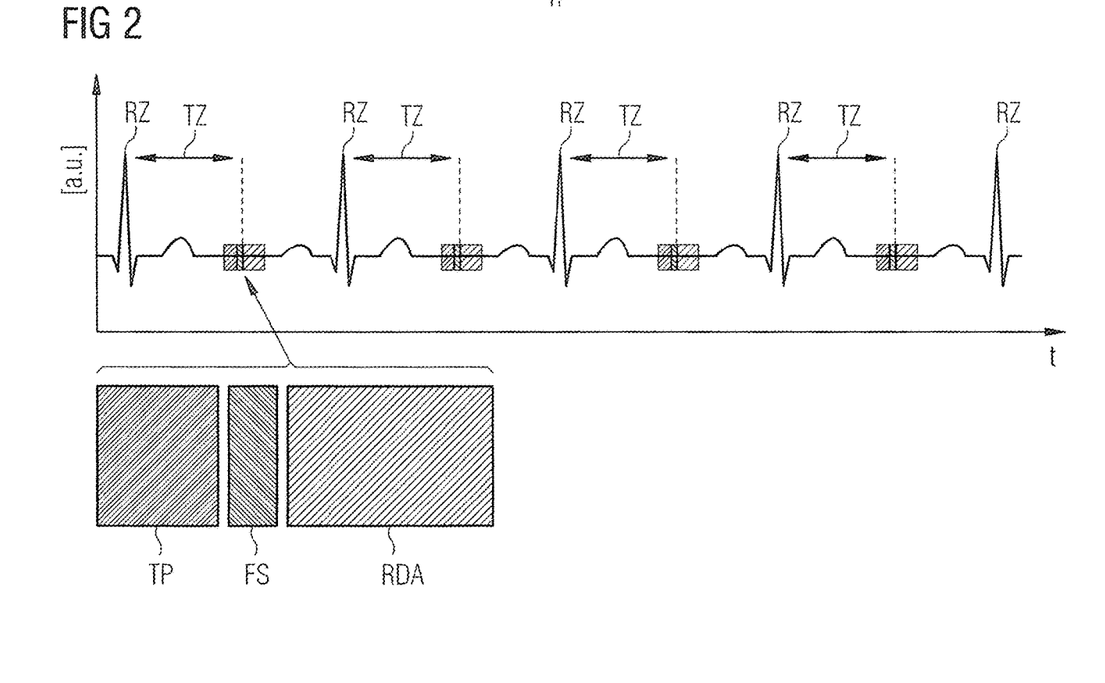
FIG. 2 schematically depicts of an EKG with a presentation of the triggering of a raw data acquisition in a diastolic phase.

FIG. 1 schematically shows the position of the heart O in the body K of the patient, and additionally also the position of the diaphragm O' which—as mentioned—marks the transition between liver and lungs and therefore is normally easily detectable in the image data at a strong light/dark transition. During breathing, the diaphragm O' in the body of the patient is continually raised and lowered, which leads to a strong displacement of the heart O within the body, predominantly in the longitudinal direction of said body (SI direction). This movement in the SI direction is thus the primary movement direction R that the heart O is subject to overall in the body K, and that thereby is shifted in the superior direction (towards the head) or in the inferior direction (towards the feet) depending on the breathing phase. The heart O itself additionally implements its own cyclical movement due to the heart beat. During a cardiac cycle, the heart thereby traverses multiple phases—known as cardiac phases. These are depicted in FIG. 2 in a schematic EKG. A cardiac cycle is typically, respectively considered from one R-spike RZ to the next R-spike RZ (the point in time of the strongest contraction of the heart). The diastolic phase, in which the heart is at rest for a relatively long period of time (namely approximately 100 ms), is located approximately in the middle region between two R-spikes RZ. This diastolic phase can thus be used in order to acquire raw data. For this, the magnetic resonance pulse sequence for raw data acquisition is triggered at the R-spike, as this is schematically represented by the trigger time period TZ in FIG. 2. For example, in a suitable magnetic resonance pulse sequence a T2 preparation TP can initially be implemented, then what is known as a fat saturator FS is emitted, and finally the actual raw data acquisition RDA takes place.

Figure 3:
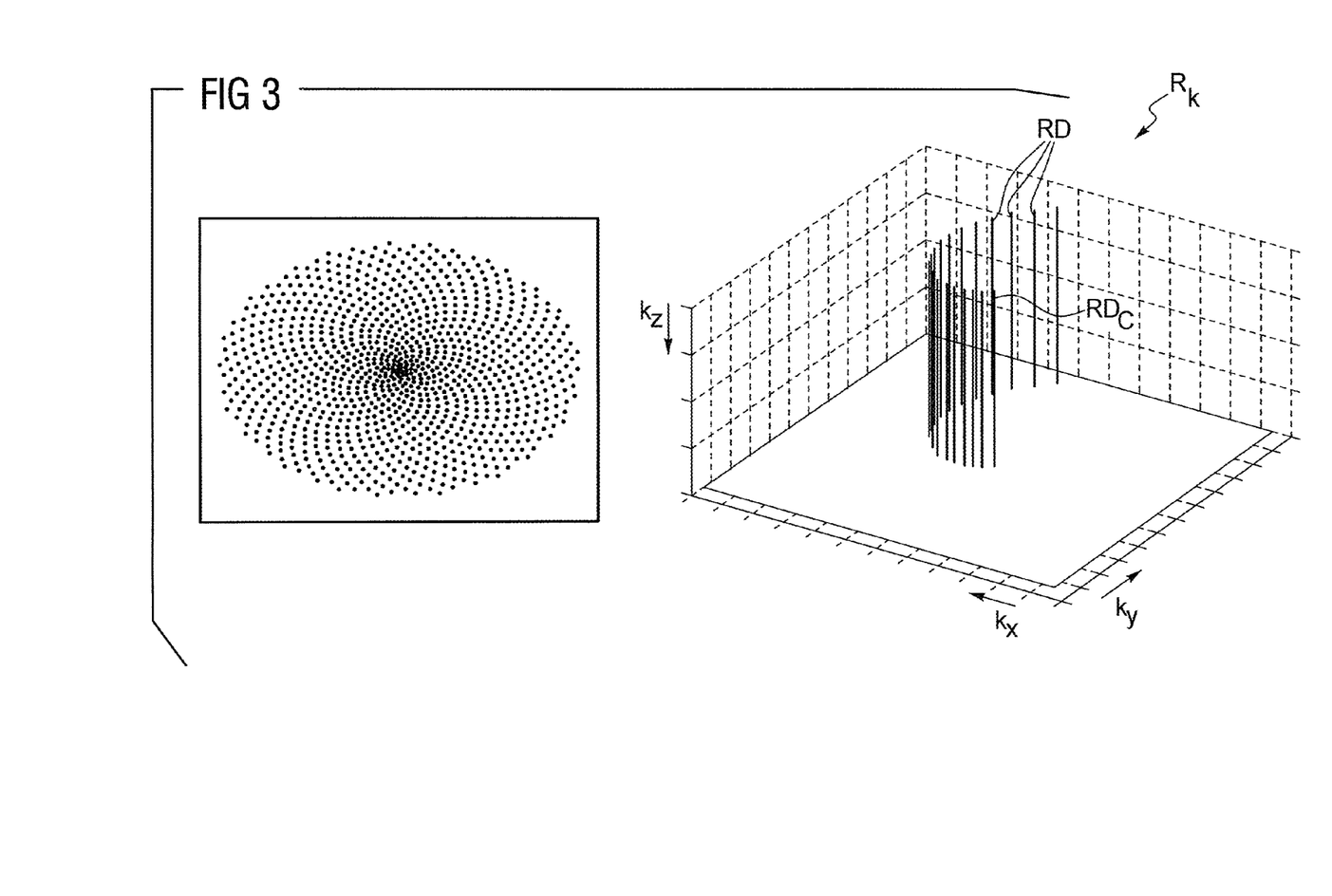
FIG. 3 depicts a k-space volume in three-dimensional Cartesian coordinates $k_x$, $k_y$, $k_z$ with a phyllotactic, spiral-shaped scan pattern (to the left is a plan view of the $k_x/k_y$ plane, and to the right is a perspective representation).

In order to "fill" (occupy) a three-dimensional k-space volume with raw data from which a 3D image data volume (the FoV) can then be reconstructed (for example with the use of a 3D Fourier transformation), multiple trajectories can be scanned (for example in Cartesian k-space $R_k$) with parallel readout processes traveling in the z-direction (in the direction of the coordinate $k_z$ in k-space). These readout processes in k-space $R_k$ are arranged in a defined pattern relative to a $k_x/k_y$ plane. One example of a trajectory given such a preferred readout type is shown in FIG. 3. Here the readout processes of the trajectories that are traveling in the z-direction are arranged according to a phyllotactic, spiral-shaped scan pattern relative to the $k_x/k_y$ plane. As can be seen on the left side in the plan view of the $k_x/k_y$ plane, the pattern consists of multiple spokes traveling radially outward from the middle point (or the middle z-axis) of k-space, which spokes are curved in a spiral shape. This is hereby a hybrid of a spiral trajectory pattern and a spoke trajectory pattern. A spiral-shaped spoke is shown on the right side in a three-dimensional perspective view. From this view it is apparent that each point of the trajectory in the $k_x/k_y$ plane represents a readout process traveling in the $k_z$ direction along which k-space is scanned in order to acquire raw data. Approximately 30 such readout processes traveling in the $k_z$ direction (which corresponds to a spiral-shaped spoke trajectory) can be implemented in the time window of a diastolic phase (100 ms). Therefore, a raw data segment can be read out as a raw data set within a diastolic phase, which raw data segment includes the raw data RF of a spiral-shaped spoke as it is schematically depicted on the right side in FIG. 3 by the set of readout processes traveling longitudinally in the $k_z$ direction. First the raw data $RD_C$ are respectively read out along the central readout process through the middle of k-space. The raw data RD are subsequently acquired along the additional readout processes, from the inside proceeding outwards. In order to sufficiently fill the k-space volume for a reconstruction of significant image data, so many raw data sets must be acquired that k-space is filled up to approximately 12%. If the required raw data of all segments are acquired, a reconstruction of the three-dimensional image data volume can take place. An acquisition of raw data can take place in a similar manner in order to acquire densely adjoining slices of the heart.

However, the heart is typically disadvantageously spatially displaced and/or deformed by the breathing movement between the acquisition of the raw data sets or segments of the k-space data in successive cardiac cycles. For a reconstruction of the image data, it is therefore necessary to produce a correction with regard to this displacement/deformation (shortened only to displacement in the following). This is possible in various ways in principle. However, for this the displacement must be at least approximately known, meaning that it must at least be determined in what breathing phase the individual raw data sets have been acquired.

Figure 4:
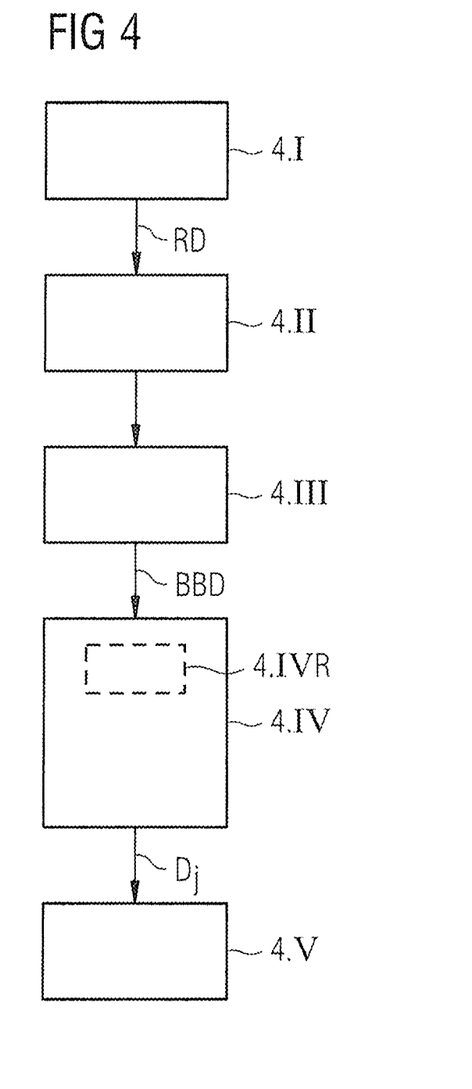
FIG. 4 is a flowchart of an embodiment of a method according to the invention for the generation of image data.

This is possible with the method presented in FIG. 4. In Step 4.I, all raw data RF are initially acquired. These are then pre-processed in Step 4.II in a special sorting algorithm (also called "binning") in order to associate them with different movement phase classes. This Step 4.II is subsequently explained in detail using FIG. 5.

For each acquired raw data set or, respectively, each raw data segment, the central raw data $RD_C$ that were acquired along the readout process of the trajectory through the k-space center (see FIG. 4) are initially transferred into image data space with the aid of a one-dimensional Fourier transformation. As a result, a one-dimensional projection—what is known as an SI projection—of the complete field of view (i.e. all image data in the FoV along the z-direction, thus in the primary direction of movement R; see FIG. 1) is obtained that is projected onto the z-axis. If it is ensured that the field of view FoV is sufficiently large that not only the heart O but also the diaphragm O' is covered (as this is depicted in FIG. 1), the light/dark transition at the diaphragm is also very easily detectable in these SI projections SIP. The SI projections SIP are thus particularly well suited as position overview data SIP.

In a first Step 5.I, a spatial scattering for these SI projections SIP that is dependent on the measurement point in time is initially determined. Such a process is illustrated with the aid of a diagram in FIG. 5. This diagram shows the individual SI projections SIP packed close next to one another, wherein the location in the z-direction along the individual SI projections SIP is plotted on the ordinate axis, and the intensity value present at a location z at a defined measurement point in time t is plotted on the abscissa axis. Here the variance $var(z(t))$ is used as a spatial measure of scattering that is dependent on the measurement point in time, meaning that the variance of a number of measurement values $z(t)$ at a defined location z is measured across multiple measurement points in time t. This variable $var(z(t))$ is shown as a function of z in the variance curve depicted on edge, immediately next to the diagram in Step 5.I. By determining the maxima and minima of this variance curve, possible test regions PR1, PR2 are selected in which a particularly high variance is present. For this, a local maximum is sought and two local minima are respectively selected in a defined interval from the found local maximum, and thus the test region is established around the maximum.

Figure 5:
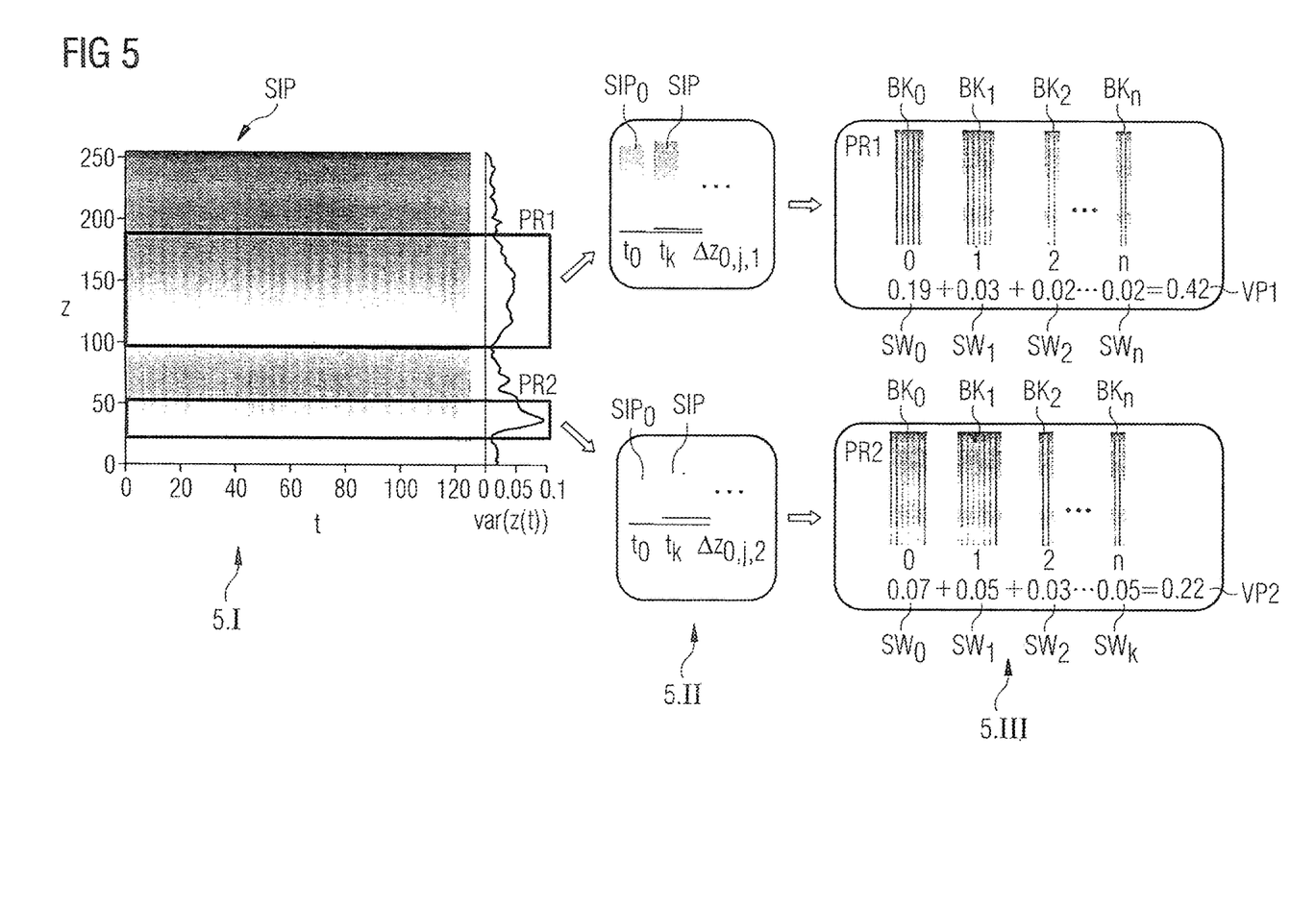
FIG. 5 depicts an example of a workflow to determine test regions in position overview data (here in the form of SI projections) and the association of the position overview data with movement phase classes.

In the case presented in FIG. 5, precisely two test regions PR1, PR2 (or, respectively, actually "test segments" of the SI projections, since the SI projections are only one-dimensional) are selected along the SI projections SIP. The one of these test regions PR1 here covers the region in which the heart O moves; the second test region PR2 here relates to a region in which the diaphragm O' moves.

In Step 5.II, deviation values of the position overview data SIP—i.e. here the SI projections SIP that were acquired at different points in time $t_k$ (k=0 to m, wherein m is the number of acquired raw data sets) from reference position overview data are then respectively, separately determined for the individual test regions PR1, PR2. Arbitrary position overview data SIP can hereby be selected as reference position overview data (or as a "reference SIP projection"). In the present case, for simplicity the SI projection acquired at the point in time t=0 in the first measurement is used as a reference SI projection $SIP_0$. To determine the deviation value of an SI projection from the reference SI projection $SIP_0$, in the individual test regions PR1, PR2 a cross-correlation of the signal relative to the reference SI projection $SIP_0$ is determined. In this way, a deviation value $\Delta z_{0,k,1}$ and $\Delta z_{0,k,2}$ is determined for every single SI projection SIP.

In Step 5.III, the individual SI projections acquired at the different points in time $t_k$ are then associated with different movement phase classes $BK_0$, $BK_1$, $BK_2$, ..., $BK_n$ on the basis of their deviation values $\Delta z_{0,k,1}$ or $\Delta z_{0,k,2}$—and in fact separately in turn for each test region PR1, PR2—wherein n is the maximum number of movement classes. For example, the movement class $BK_0$ corresponds to a deviation value of +0.5 to a maximum of −0.5; the movement class $BK_1$ corresponds to a deviation value between −0.5 and a maximum of −1.5 etc. The polarity or the allowed deviation values for the individual movement phase classes $BK_0$, $BK_1$, $BK_2$, ..., $BK_n$ can be freely selected in principle. In the present case, they are selected so that a first acquisition takes place at the point in time t=0 when the patient has completely exhaled, and thus the diaphragm in the body K is situated all the way at the top. The deviations in the additional breathing phases are thus characterized by a displacement in the negative z-direction, downward toward the feet.

In the movement class $BK_0$, all SI projections SIP (and naturally the associated additional raw data) are thereby associated with the same raw data set or segment in which only a minimal deviation from the reference SI projection $SIP_0$ has been established in the respective test region PR1 or PR2. This deviation increases with the increasing number of the class, meaning the further distant the acquisition of the movement phase in which the reference SI projection $SIP_0$ was acquired. Since this sorting for the two test regions PR1, PR2 has been conducted separately, it can result that—according to the sorting—in the first test region PR1 an SI projection and the associated raw data have been classified in the same movement class $BK_0$ as the reference SI projection, and within the second test region PR2 a classification of the same raw data in a class deviating from this (for example the neighboring class $BK_1$) takes place.

In principle, it is to be assumed that the signal variations of the SI projections that are acquired in the same breathing phase or movement phase within the breathing cycle should be relatively slight. Furthermore, if the global variations are minimal, this should likewise apply to each sub-interval within the SI projections. Therefore, it can be assumed that the detection of the breathing movements and the classification of the SI projections or associated raw data into the individual movement phase classes $BK_0$, $BK_1$, $BK_2$, ..., $BK_n$ can take place most reliably in that one of the two test regions PR1, PR2 in which the least variations are present within said movement phase classes $BK_0$, $BK_1$, $BK_2$, ..., $BK_n$. Therefore—as this is also depicted in Step 5.III in FIG. 5—the time-dependent spatial variance of the SI projection SIP in the individual test regions PR1, PR2 is still determined. This variance determination takes place analogous to the procedure in Step 5.I, but now separately for the SI projections in the individual movement phase classes $BK_0$, $BK_1$, $BK_2$, ..., $BK_n$. In other words: a separate scattering value $SW_0$, $SW_1$, $SW_2$, ..., $SW_n$ is determined for each movement class $BK_0$, $BK_1$, $BK_2$, ..., $BK_n$.

These scattering values $SW_0$, $SW_1$, $SW_2$, ..., $SW_n$ are then separately totaled up for each test region PR1, PR2 in order to thus obtain a separate trust parameter value VP1, VP2 for each of the test regions PR1, PR2. As this is depicted in FIG. 5, here at 0.22 the trust parameter value $VP_2$ for the second test region PR2 is significantly lower than the trust parameter value $VP_1$—which is 0.42—for the test region PR2. It is thus to be assumed that a more reliable detection of the movement was possible in the test region PR2. Therefore, the sorting of the individual raw data into the movement phase classes $BK_0$, $BK_1$, $BK_2$, ..., $BK_n$ that is determined in test region PR2 is used for the additional reconstruction or correction of the raw data with regard to the breathing movement.

Astonishingly, it has turned out that the initially implemented automatic identification of possible good test regions PR1, PR2, and a subsequent automatic check of which of these test regions PR1, PR2 has the highest reliability, and the subsequent use of the classification according to this most reliable test region PR1, PR2, leads to a dramatic improvement of the method relative to a method in which a test region is simply established at the beginning.

Using this classification or using the deviation values $\Delta z_{0,k,2}$ that are determined in Step 5.II, a reconstruction of the image data from the raw data can then take place in an arbitrary manner in order to generate images that are largely free of movement artifacts. For example, for this the method used in the document by Piccini et al. can be used. However, the modified method explained in the following is preferably used for this.

Given a scanning of three-dimensional k-space with the phyllotactic, spiral-shaped scan pattern described in the following (as is shown in FIG. 3), a relatively large amount of raw data can in fact be determined in a defined, predetermined acquisition time in order to reconstruct image data from these. On the other hand, however, a relatively severe undersampling is still required in order to be able to implement the acquisition of a complete volume of an organ (the heart, for instance) in an acceptable total measurement time.

Therefore, it is desirable if not only a smaller portion of the acquired raw data—for example only raw data from the movement class $BK_0$ in a movement state given full inhalation (in this phase, the heart movement spends a relatively long time in a type of rest phase)—is used, but rather as many raw data as possible, particularly preferably all acquired raw data. However, for this the raw data must be corrected in the reconstruction as explained with regard to their displacement relative to one another. From the sorting method above it is already known which raw data were acquired in which movement phases. For this, the raw data were already classified in movement phase classes. However, it is not known how the raw data acquisition in the different movement classes/phases actually affects the displacement of the raw data or the reconstructed image data.

A reconstruction of image data from the complete raw data under consideration of the displacement of the spatial structures due to the breathing movement can be implemented with the use of an iterative numerical optimization method (such as a quasi-Newton method), which is particularly suitable for CS (compressed sensing) data. This can be a nonlinear optimization method in which the operations are implemented relatively quickly per pixel, and thereby the following cost function is minimized:

$$\operatorname*{argmin}_{x} \sum_{j} \sum_{i} \|M_j F C_i D_j x - y_{i,j}\|_2^2 + \lambda |x|_{TV} \quad (1)$$

In this cost function, the vector x represents the image data and the vector $y_{ij}$ represents the raw data that were acquired with a coil i in a breathing or, respectively, movement phase j. $C_i$ is the coil sensitivity of the i-th coil (in matrix form). $D_j$ represents the deformation field (in matrix form), i.e. is hereby the model which represents the movement during the acquisition of the data $y_{ij}$. F is the Fourier transformation operator. $M_i$ represents in matrix form the scan pattern for the respective movement phase j. The summation takes place over the square of the Euclidean norm. The additional term $\lambda |x|_{TV}$ (TV=total variation) is a normalization term that increases the costs for deviations that are too large, and thus ensures a sufficient convergence of the method. The factor A can in principle be chosen arbitrarily; it should advantageously be between 0 and 1. Among other things, it depends on the scaling of the measurement data.

However, in order to be able to operate with this method, the movement field $D_j$ for each breathing phase j must be known. For this purpose, in the method depicted in FIG. 4 interim image data BBD for the individual movement phases or the movement phase classes determined with the aid of the method described above are initially reconstructed in Step 4.III. This can respectively take place again with a quasi-Newton optimization method, but now the following target function is used:

$$\operatorname*{argmin}_{x} \sum_{i} \|W(MFC_i x - y_{i,j})\|_2^2 + \lambda |x|_{TV} \quad (2)$$

As is apparent, this target function no longer includes summation over different movement phases j. Instead of this, here a weighting factor W (likewise in matrix form) is introduced. With the aid of this weighting factor W, it is ensured that acceptable interim image data can be determined for a single movement phase, wherein not only are the raw data of exactly the associated movement phase class used, however, but also raw data from other (in particular directly or indirectly adjacent) movement phase classes. However, the raw data from the other movement phase classes are thereby weighted corresponding to the weighting W so that raw data that were acquired from movement phases far distant from the actual desired movement phase incur only a very slight weighting in relation to the raw data from the actual desired movement phase.

Figure 6:
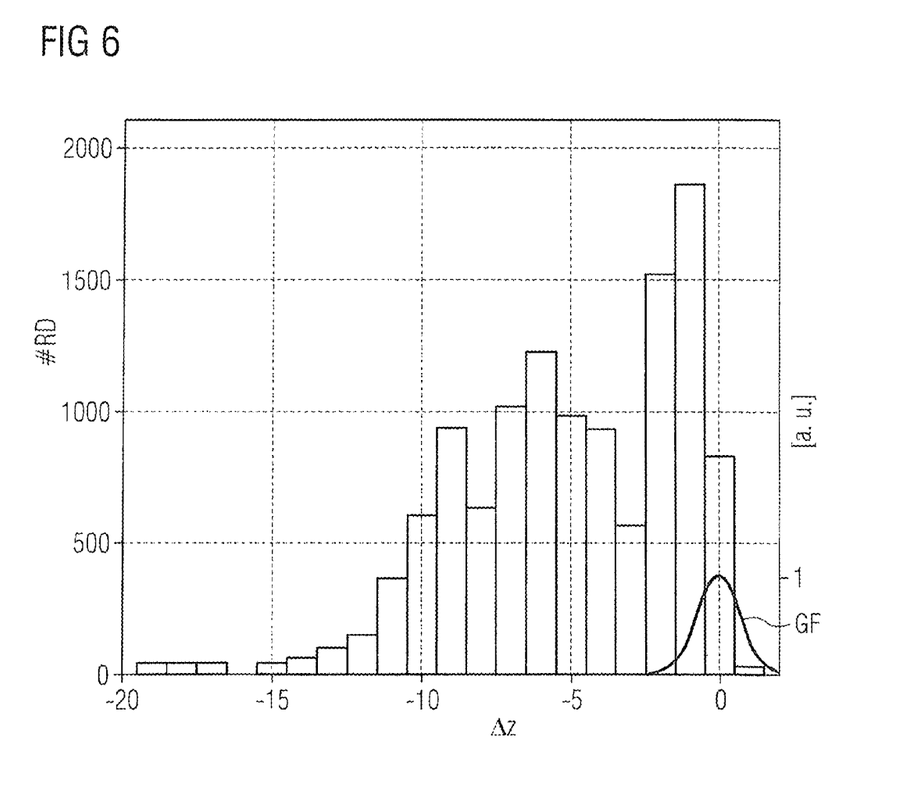
FIG. 6 is a histogram for the number of acquired raw data sets for different movement phase classes.

For example, a Gaussian weighting can be used as a suitable weighting function. This is schematically depicted in FIG. 6. Here the number #RD (see the left vertical axis of the diagram) of acquired raw data sets or, respectively, segments is plotted over the detected deviation Δz of the respective raw data set in a histogram. The columns of the histogram thus correspond here to the movement phase classes, wherein the movement phase class $BK_0$ is represented by the column around the value Δz=0 and the movement phase class $BK_5$ is represented by the column around the value Δz=5, etc.

Moreover, here a weighting function GF (scaled to a maximum of 1 in arbitrary units; see right vertical axis of the diagram)—concretely a Gaussian function—is drawn with which it is visualized which relative weighting the raw data from the different movement phase classes incur when an image for a defined movement phase j (corresponding to a defined movement phase class) should be reconstructed according to Formula (2). As can be seen, the raw data of the movement phase class of the desired movement phase (here the movement phase class $BK_0$) go to a maximum of 1, and the Gaussian function GF declines relatively strongly, such that essentially only the raw data of the directly adjacent movement phase class (and possibly in small part the raw data of the next movement phase class but one) are still used. It should be noted that such a weighting can not only be implemented with regard to the movement phase classed, but also a weighting of every single raw data set based on its exact deviation value Δz (which was determined with the method described using Step 5.II in FIG. 5) can also be implemented. This means that, in the creation of the interim image data BBD for a defined movement phase, every single raw data set is considered according to an individual weighting value that is respectively provided by the weighting function GF. With this method, it is ensured that sufficient raw data in order to reasonably determine significant interim image data for this movement phase are always present, even for movement phases in which only relatively little raw data could be generated.

If the interim image data BBD for all desired movement phases or movement phase classes have been generated in Step 4.III (see FIG. 4), in Step 4.IV deviation data $D_j$ of the individual interim image data are determined, meaning that the deformation field or, respectively, movement field $D_j$ for the individual movement phases are calculated.

For this purpose, in Step 4.IV R of one of the generated interim image data sets is initially selected as a reference image data set. This is that image data set for which the most raw data were available. For example, these could be the raw data as they are presented in the histogram in FIG. 6, or the interim image data set that was created for the movement phase with a deviation by Δz=1 (meaning Δz between −0.5 and −1.5), or for the movement phase class $BK_1$. The deviation data or the deformation field $D_j$ is then determined using a registration of the image data set of the respective movement phase j with the reference interim image data set of the reference movement phase. A non-rigid, symmetrical, diffeomorphic image registration is preferably used. For example, such a registration method is explained in the publication by Avants, B. B. et al., "Symmetric diffeomorphic image registration with cross-correlation: Evaluating automated labeling of elderly and neurodegenerative brain", MedIA 12: 26 to 41, (2008), the content of which is inasmuch referenced here. If the movement field $D_j$ has been determined in this manner for each movement phase j, the reconstruction of the desired image data BD can take place in step 4.V with the target function (1) explained above using all raw data, and in fact independent of in which breathing movement phase they were acquired.

Figure 7:
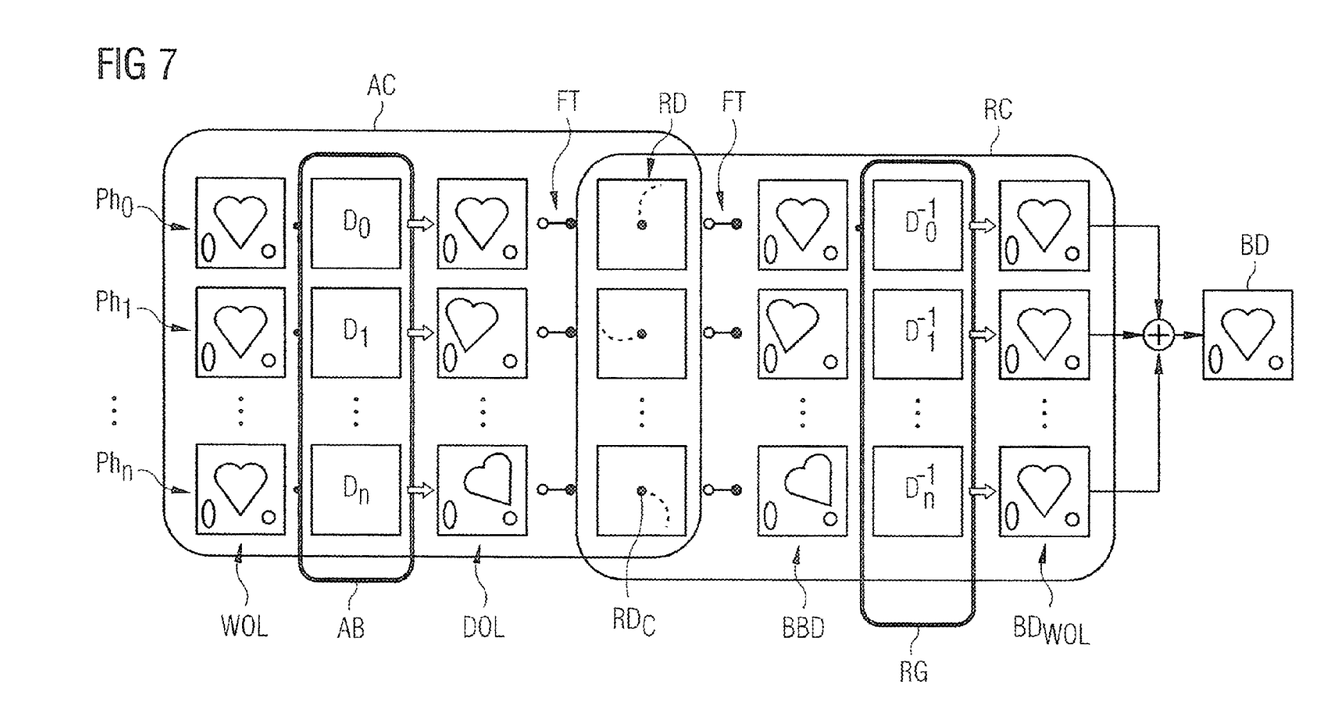
FIG. 7 schematically depicts an example of a procedure for the reconstruction of image data from raw data of different movement phases.

The determination of the deformation field $D_j$ is graphically illustrated again using FIG. 7. The breathing movement—and the deformation or displacement of the heart position that is thereby generated—is depicted on the left side in the data acquisition step AQ. The upper row shows the one first movement phase $Ph_0$, the second row shows a second movement phase $Ph_1$, and the lowermost row shows a last movement phase $Ph_n$. Normally, the same object position WOL as is depicted in the first column would be provided without these movement phases or, respectively, without the breathing movement. However, due to the breathing movement AB a deformation takes place which is different in the individual movement phases $Ph_0, Ph_1, \ldots, Ph_n$, and which can respectively be described by a deformation field or, respectively, movement field $D_0, D_1, \ldots, D_n$. This then leads to a subject position DOL that is deformed in the individual phases $Ph_0, Ph_1, \ldots, Ph_n$ relative to one another. This deformation is also noticeable in the raw data RD in k-space. The discontinuity (jump) in k-space here is schematically depicted via the Fourier transformation FT. However, in k-space the acquisition of different raw data segments RD takes place in the individual phases $Ph_0, Ph_1, Ph_n$, wherein in each segment a readout process through the k-space center RDC is also determined at least once. These raw data sets RD can then be transferred again into image data space in a reconstruction step RC with a Fourier transformation FT, wherein interim image data BBD which respectively show the subject in the deformed subject position DOL are created if only the raw data RD from a single movement phase $Ph_0, Ph_1, \ldots, Ph_n$ are taken into account or—as described above—are weighted corresponding to the desired movement phases $Ph_0, Ph_1, \ldots, Ph_n$. The deformations or, respectively, displacements—more precisely stated, the deformation fields $D_0, D_1, \ldots, D_n$ as well as the associated inverse deformation fields $D_0^{-1}, D_1^{-1}, \ldots, D_n^{-1}$ that are generated via the breathing movement AB—that are used in the target function (1) can then be calculated via the described registration of the interim image data BBD. If the inverse deformation fields $D_0^{-1}, D_1^{-1}, \ldots, D_n^{-1}$ were applied to the interim image data BBD, the deformation would theoretically be canceled out, and image data $BD_{WOL}$ for different movement phases $Ph_0, Ph_1, \ldots, Ph_n$ would be generated in the same subject position, which could then yield the image data BD overall. However, in connection with this it is noted again that the procedure shown in FIG. 7 merely schematically explains the principle, and that the mathematical reconstruction of the desired corrected image data BD advantageously takes place with the target functions (1) and (2) as explained above, with the use of the numerical quasi-Newton optimization method.

Figure 8:
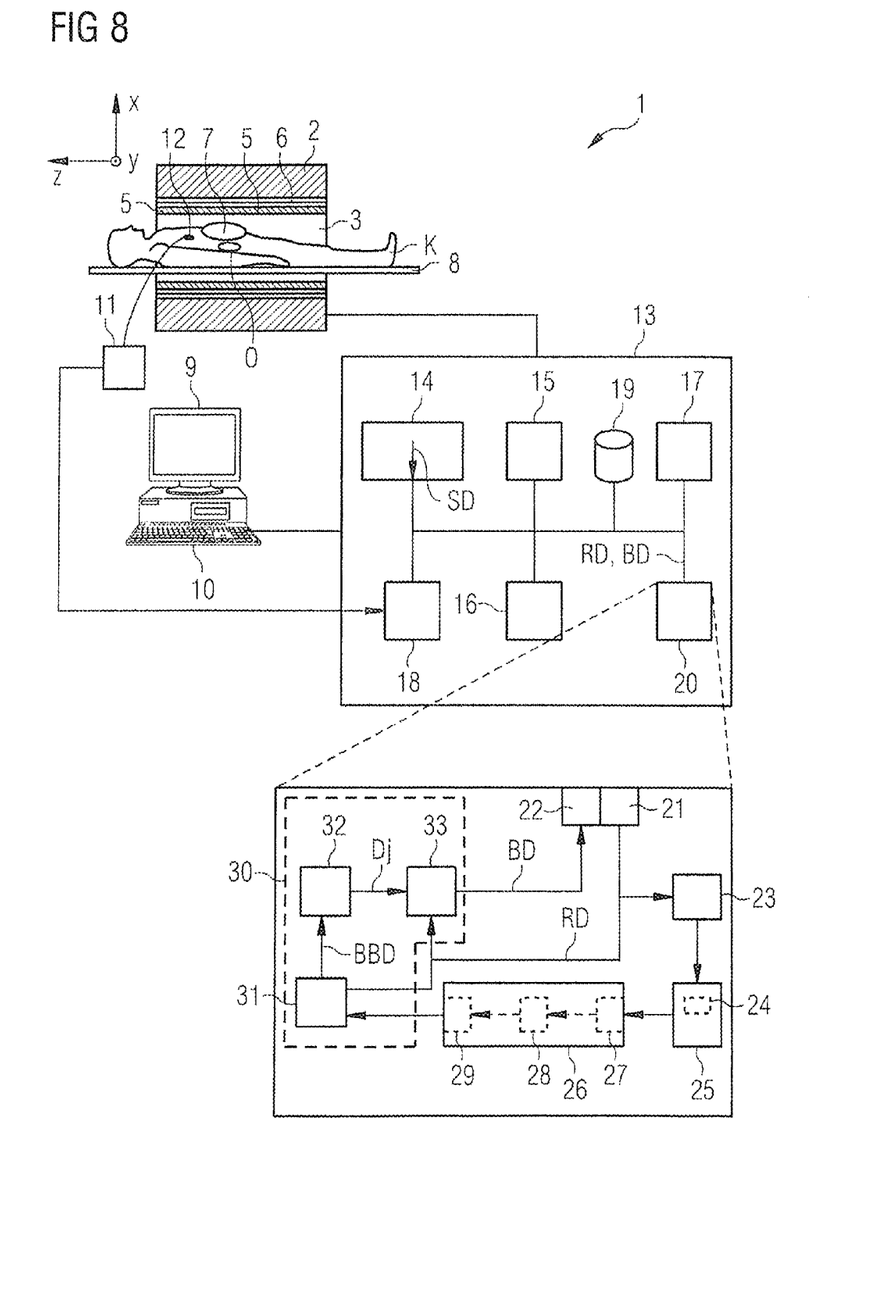
FIG. 8 schematically depicts a magnetic resonance system with an image data generation device according to one exemplary embodiment of the invention.

A magnetic resonance system 1 (also "MR system" in the following) according to the invention with which the method according to the invention can be implemented is schematically depicted in FIG. 8. This system 1 includes the actual magnetic resonance scanner 2 with a measurement space or patient tunnel extending in the z-direction, into which measurement space 3 or patient tunnel is driven a patient or test subject on a bed 8, in whose body K is located the examination subject O (here the heart).

The magnetic resonance scanner 2 is typically equipped with a basic field magnet system 4, a gradient system 6 as well as an RF transmission antenna system 5 and an RF reception antenna system 7.

In the shown exemplary embodiment, the RF transmission antenna system 5 is a whole-body coil permanently installed in the magnetic resonance scanner 2, in contrast to which the RF reception antenna system 7 includes local coils (symbolized by only a single local coil in FIG. 1) to be arranged on the patient or, respectively, test subject. In principle, however, the whole-body coil can also be used as an RF reception antenna system and the local coils can be used as an RF transmission antenna system insofar as these coils can be switched into different operating modes.

Furthermore, the MR system 1 has a central control device 13 that is used to control the MR system 1. This central control device 13 comprises a sequence control unit 14 for pulse sequence control. With this, the sequence of radio-frequency pulses (RF pulses) and the gradient pulses is controlled depending on a selected magnetic resonance measurement sequence. For example, the control parameters for the magnetic resonance measurement sequence can be predetermined within a measurement or control protocol. For example, multiple measurement or control protocols are stored in the memory 19 for selection by an operator and are modifiable.

To output the individual RF pulses, the central control device 13 has a radio-frequency transmission device 15 that generates the RF pulses, amplifies them and feeds them into the RF transmission antenna system 5 via a suitable interface (not shown in detail). The radio-frequency transmission device can include multiple of components, among other things low-level signal generators which ensure that that the matching radio-frequency pulses are initially generated with low amplitude, and suitable radio-frequency amplifiers in order to feed the radio-frequency pulses into the antennas with the necessary power. Also belonging among these are monitoring components with which it is ensured that the radio-frequency power lies within the limit values predetermined by the SAR (SAR=Specific Absorption Rate) standards, etc.

To control the gradient coils of the gradient system 6, the control device 13 has a gradient system interface 16. With the use of the components of this interface, the required gradient pulses are generated and then fed into the various gradient coils of the gradient system or the desired gradient voltages are applied to the gradient coils.

The sequence control unit 14 communicates in a suitable manner (for example via emission of sequence control data SD) with the radio-frequency transmission device 15 and the gradient system interface 16 to emit the pulse sequences.

Moreover, the control device 13 has a radio-frequency reception device 17 (likewise suitably communicating with the sequence control unit 14) in order to acquire magnetic resonance signals (i.e. raw data) received in coordination by the RF reception antenna system 7. The radio-frequency reception device accordingly has a number of reception channels in which the magnetic resonance signals captured by the individual antennas of the reception antenna system (and possibly additional, pre-processed magnetic resonance signals) are accepted and processed further, in particular are amplified and digitized.

Since here the acquisition of the raw data respectively takes place at a matching point in time, and raw data should always be acquired only in the diastolic phase of the heart, the central control device 13 also has an EKG interface 18 that is connected with an EKG device 11 to which the patient is connected with typical electrodes 12. As is shown in FIG. 2, the EKG curve is monitored with this and a trigger command is always output at the matching point in time after an R-spike RZ, such that the acquisition is started precisely at the correct point in time and is also ended again at the corrected point in time. Here it can also be established whether the diastolic phase was maintained during the entire acquisition of the raw data or—for example—whether the diastolic phase was too short due to heart rhythm fluctuations. In this case, the raw data can then be discarded.

An image data generation unit 20 accepts the acquired raw data RD and generates the desired magnetic resonance image data BD of the subject O from these in the procedure explained above. For example, these can be stored in a memory 19 or be output to a user.

To generate the image data BD in the explained procedure, the image data generation unit 20 initially has a raw data interface 21 via which the raw data RD are accepted. In an overview data generation unit 23, the position overview data (or here the SI projections) are then generated that are then passed to an overview data analysis unit 24 that determines the scattering of the position overview data. This overview data analysis unit 24 here is part of the test region selection unit 25, which (as explained above using FIG. 5) selects potential spatial test regions (i.e. the SI projection segments PR1, PR2) on the basis of the scattering. The individual test regions PR1, PR2 are then evaluated in the manner described above in a trust parameter value determination unit 26. For this, in a classification unit 27 the deviation values $\Delta z$ of the position overview data (i.e. the SI projections) are initially determined relative to the reference position overview data, and based on these the position overview data and the associated raw data are then classified in the movement phase classes. The calculation of the scattering (in particular the variance) of the respective position overview data classified in the individual movement phase classes then takes place in a scatter value determination unit 28, and finally the sum of the variances of the individual movement phase classes is calculated in an adder unit 29 in order to then arrive at a trust parameter value VP1, VP2 for each test region PR1, PR2. In this way, a test region is verified within the trust parameter value determination unit 26. Finally, the information about the classifications of the raw data into the individual movement phase classes are transmitted to a reconstruction unit 30 that then reconstructs the desired image data BD on the basis of the raw data, under consideration of this information. This reconstruction unit 30 on the one hand comprises an interim reconstruction unit 31 with which—as described above—interim image data sets BBD are initially generated for each movement phase or movement phase class, which interim image data sets BBD are then passed to a deviation data determination unit 32. This determines the deviation data $D_j$ or, respectively, movement fields of the interim image data relative to the reference image data. The deviation data or the movement fields $D_j$ that are thereby determined are then passed to an overall reconstruction unit 33 that then reconstructs the desired image data BD using all raw data, for example using the target function (1). These image data BD can then be output again via an image data interface 22 and, for example, can be stored in a memory 19 and/or be output to a screen 9. These image data BD can likewise also be stored in external memories via a network and/or be output to corresponding output devices or, respectively, to a monitor for finding.

An operation of the central control device 13 can take place via a terminal with an input unit 10 and a display unit 9, via which terminal the entire MR system 1 can thus also be operated by an operator. The image data BD can also be displayed at the display unit 9, and measurements can be planned and started by the input unit 10, in combination with the display unit 9 if necessary.

Moreover, the MR system 1—and in particular the control device 13—can have a plurality of additional components that are not shown in detail here but that are typically present at such apparatuses, for example a network interface in order to connect the entire system with a network and in order to be able to exchange raw data and/or image data or, respectively, parameter maps, but also additional data (for example patient-relevant data or control protocols).

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to generate image data representing a moving object inside of an examination subject, comprising:
   operating an image data acquisition device to acquire raw data in the frequency domain, at respectively different acquisition points in time, from a region of an examination subject comprising a moving object, said points in time respectively occurring in different movement phases of movement of said moving object;
   providing said raw data to a computerized processor and, in said processor, reconstructing a plurality of interim image data sets in the spatial domain that are respectively associated with said different movement phases of the moving object, by performing a first Fourier transformation of the respective raw data acquired during said different movement phases at said different acquisition points in time;
   in said processor, determining deviation data between said interim image data sets for said respective different movement phases, said deviation data representing deviations in the spatial domain between respective interim image data sets that result from said movement of said moving object; and
   in said processor, reconstructing diagnostic image data by performing a second Fourier transformation, dependent on said deviation data, of the respective raw data acquired during said different movement phases at said different acquisition points in time, and making the reconstructed diagnostic image data available in electronic form at an output of the processor.

2. The method as claimed in claim 1 comprising, in said processor, differently weighting the respective raw data acquired at said different movement phases, when reconstructing said different image data sets, and setting the respective weighting dependent on the movement phase of the object in which the respective raw data were acquired.

3. The method as claimed in claim 2 comprising setting said weighting dependent on a distance from a predetermined movement phase for which the respective interim image data sets are reconstructed.

4. The method as claimed in claim 1 comprising, in said processor, associating the respective raw data with different movement phase classes.

5. The method as claimed in claim 4 comprising reconstructing said interim image data sets for respectively different movement phase classes, with respective weightings dependent on the respective movement phase class associated with the raw data being reconstructed.

6. The method as claimed in claim 5 comprising setting said weightings using a weighting function wherein raw data for the movement phase class associated with respective raw data being reconstructed is given a higher weighting than raw data of other movement phase classes.

7. The method as claimed in claim 1 comprising reconstructing said interim image data using an iterative numerical optimization method.

8. The method as claimed in claim 7 comprising using a quasi-Newton method as said iterative numerical optimization method.

9. The method as claimed in claim 1 comprising, in said processor, generating position overview data for the respective measurement points in time from at least a portion of said raw data, and associating respective raw data with different movement phase classes based on said position overview data.

10. The method as claimed in claim 9 comprising determining said deviation values from said position overview data with respect to reference position overview data, and associating the raw data with respectively different movement phase classes dependent on the deviation values.

11. The method as claimed in claim 1 wherein the examination subject exhibits a breathing movement, and wherein said movement phases are respective phases in a respiratory cycle.

12. An image data generation device to generate image data representing a moving object inside of an examination subject, comprising:
   an image data acquisition device configured to obtain or receive raw data in the frequency domain, acquired at respectively different acquisition points in time, from a region of an examination subject comprising a moving object, said points in time respectively occurring in different movement phases of movement of said moving object;
   a computerized processor provided with said raw data, said processor being configured to reconstruct a plurality of interim image data sets in the spatial domain that are respectively associated with said different movement phases of the moving object, by performing a first Fourier transformation of the respective raw data acquired during said different movement phases at said different acquisition points in time;
   said processor being configured to determine deviation data between said interim image data sets for said respective different movement phases, said deviation data representing deviations in the spatial domain between respective interim image data sets that result from said movement of said moving object; and
   said processor being configured to reconstruct diagnostic image data by performing a second Fourier transformation, dependent on said deviation data, of the respective raw data acquired during said different movement phases at said different acquisition points in time, and to make the reconstructed diagnostic image data available in electronic form at an output of the processor.

13. A magnetic resonance apparatus comprising:
   a magnetic resonance data acquisition unit;
   a control unit configured to operate the magnetic resonance data acquisition device to acquire raw data in the frequency domain, at respectively different acquisition points in time, from a region of an examination subject comprising a moving object, said points in time respectively occurring in different movement phases of movement of said moving object;
   a computerized processor provided with said raw data, said processor being configured to reconstruct a plurality of interim image data sets in the spatial domain that are respectively associated with said different movement phases of the moving object, by performing a first Fourier transformation of the respective raw data acquired during said different movement phases at said different acquisition points in time;

said processor being configured to determine deviation data between said interim image data sets for said respective different movement phases, said deviation data representing deviations in the spatial domain between respective interim image data sets that result from said movement of said moving object; and said processor being configured to reconstruct diagnostic image data from said by performing a second Fourier transformation, dependent on said deviation data, of the respective raw data acquired during said different movement phases at said different acquisition points in time, and to make the reconstructed diagnostic image data available in electronic form at an output of the processor.

14. A non-transitory, computer-readable data storage medium encoded with programming instructions, said storage medium being loaded into a computerized control and evaluation system of an imaging apparatus, said programming instructions causing said control and evaluation system to:

receive raw data, acquired in the frequency domain at respectively different acquisition points in time, from a region of an examination subject comprising a moving object, said points in time respectively occurring in different movement phases of movement of said moving object;

reconstruct a plurality of interim image data sets in the spatial domain that are respectively associated with said different movement phases of the moving object, by performing a first Fourier transformation of the respective raw data acquired during said different movement phases at said different acquisition points in time;

determine deviation data between said interim image data sets for said respective different movement phases, said deviation data representing deviations between respective interim image data sets that result from said movement of said moving object; and reconstruct diagnostic image data by performing a second Fourier transformation, dependent on said deviation data, of the respective raw data acquired during said different movement phases at said different acquisition points in time, and make the reconstructed diagnostic image data available in electronic form at an output of the processor.

* * * * *